United States Patent [19]

Williamson, IV et al.

[11] Patent Number: 4,888,004
[45] Date of Patent: Dec. 19, 1989

[54] METHOD AND APPARATUS FOR PURGING TUBING NETWORK OF BLOOD PROCESSING SYSTEM

[75] Inventors: Warren P. Williamson, IV, Huntington Beach; Paul R. Prince, Fountain Valley, both of Calif.

[73] Assignee: HemaScience Laboratories, Inc., Santa Ana, Calif.

[21] Appl. No.: 49,029

[22] Filed: May 13, 1987

Related U.S. Application Data

[63] Continuation of Ser. No. 804,846, Dec. 5, 1985, abandoned.

[51] Int. Cl.⁴ .............................................. A61M 3/00
[52] U.S. Cl. ...................................... 604/45; 604/151; 604/280
[58] Field of Search ................ 604/45, 122, 123, 126, 604/4–6, 30, 34, 44, 45, 124, 125, 174, 411–412, 414–415, 905, 280, 151; 128/DIG. 26

[56] References Cited

U.S. PATENT DOCUMENTS

| | | | |
|---|---|---|---|
| 2,309,302 | 1/1943 | Butler et al. | 604/34 |
| 2,452,643 | 11/1948 | Fields | 604/905 |
| 2,817,372 | 12/1957 | Barr, Sr. et al. | 604/411 |
| 2,833,281 | 5/1958 | Krug | 604/411 |
| 3,017,885 | 1/1962 | Robicsek | 604/4 |
| 3,626,938 | 12/1971 | Versaci | 604/122 |
| 3,833,013 | 9/1974 | Leonard | 604/122 |
| 4,177,808 | 12/1979 | Malbec | 604/122 |
| 4,209,013 | 6/1980 | Alexander et al. | 604/29 |
| 4,347,874 | 9/1982 | Sullivan et al. | 604/30 |
| 4,428,743 | 1/1984 | Heck | 604/4 |
| 4,445,884 | 5/1984 | Kurtz et al. | 604/317 |
| 4,447,237 | 5/1984 | Frisch et al. | 604/175 |
| 4,509,861 | 4/1985 | Sjönell | 604/183 |
| 4,636,196 | 1/1987 | Tsuji et al. | 604/122 |
| 4,643,713 | 2/1987 | Viitala | 604/122 |

Primary Examiner—C. Fred Rosenbaum
Assistant Examiner—Kathleen A. Daley
Attorney, Agent, or Firm—Nixon & Vanderhye

[57] ABSTRACT

Method and apparatus for purging air from a tubing network finds particular utility as a component part of a blood constituent processing system. Collection and return needles of a disposable tubing network are initially contained within a common antiseptic enclosure. A purge fluid (e.g., saline solution) may then be introduced into the interior chamber of the enclosure via one of the needles and withdrawn from the interior chamber via the other of the needles. Air entrained in the tubing network may thus be trapped within the common enclosure itself and/or vented therefrom via a one-way valve and hydrophobic microbe filter and/or the entrained air pockets may be encouraged to flow to a separate suitable air trap location of the tubing network whereby the network is purged of air.

19 Claims, 2 Drawing Sheets

METHOD AND APPARATUS FOR PURGING TUBING NETWORK OF BLOOD PROCESSING SYSTEM

This is a continuation of application Ser. No. 804,846 filed Dec. 5, 1985 now abandoned.

FIELD OF INVENTION

The present invention generally relates to method and apparatus for purging air from a disposable tubing set (e.g., of the type used in a blood constituent processing system which both withdraws and returns blood constituents from/to a patient). It also generally relates to method and apparatus for maintaining the needle(s) of such a system in a sterile or antiseptic environment until actual usage.

BACKGROUND AND SUMMARY OF THE INVENTION

Conventional blood constituent processing systems typically utilize a disposable flexible tubing network (including connected related devices) for withdrawing blood from a donor, processing the blood (for example, to separate a desired blood constituent) and then returning processed blood constituents to the patient or donor. Blood constituent processing systems may, for example, be of the type which pass blood through a constituent separating device so as to obtain concentrated blood plasma and/or platelet constituents while returning residual blood constituents to the donor or making them available for other uses. While some systems use a single needle for withdrawal and return (e.g., on a time muliplexed basis), others use a pair of needles—one for withdrawal and one for return.

In such blood processing systems, it is, of course, necessary that air be purged from the tubing network prior to connection to a human patient or donor. It would also be advantageous for air to be purged automatically (as by the execution of a suitable computer program which effects control over fluid pumps, valves, etc., operatively acting on the network after its installation in a host machine) to minimize the phlebotomist's tasks.

Until the present invention, one conventional purge procedure has been simply to pass a purge fluid (i.e., a saline solution) through the tubing network until the fluid is discharged from the distal end of the collection/return needles with the discharged fluid being collected in a suitable waste receptacle. The saline solution is discharged from the needles until the phlebotomist is satisfied that all air has been purged in the upstream tubing network. This is not only a messy and wasteful procedure, it also necessarily exposes the needle to a nonsterile atmosphere throughout the procedure.

It is also known to provide a single tubular needle with a frangible sheath including a porous biological filter of the type which is permeable to gas (e.g., air) yet hydrophobic and thus impermeable to liquid (e.g., saline solution and/or blood). While enclosing a single needle with a biological filter/sheath may be adequate for relatively simple tubing networks—that is, tubing networks having few, if any, branches and/or flow paths—such a conventional system is inadequate for a relatively complex tubing network having numerous branches and/or flow paths which must be purged of air prior to use. The possibility exists in complex tubing networks for multiple "pockets" of air to be interspersed with the saline purge liquid. Thus, once an advance column of purge liquid reaches the biological filter sheath, air entrained upstream will not be permitted to reach the filter (and thus be purged from the tubing network) since the advance liquid column will, in effect, "lock" further flow towards the filter due to its impermeability to liquid.

To alleviate this problem and thus ensure complete air purging, it has been prior practice to circulate saline in a portion of the tube set and then to simply remove the biological filter/sheath so as to permit remaining upstream columns of saline liquid (and thus the remaining pockets of entrained air) to be discharged from the needle. Accordingly, for all intents and purposes, there only one conventional method of removing remaining pockets of entrained air from a complex tubing network—that is, by simply allowing a sterile liquid (e.g., saline) to freely flow through the tubing network and be discharged from the needle for a time sufficient to ensure complete air purging.

Prolonged exposure of the collection/return needles to a nonsterile environment is, for obvious reasons, undesirable. Yet the prior practices described above tend to exacerbate potential contamination of the needle since exposure to a nonsterile environment occurs during much of the purging cycle—and may continue even thereafter if the patient/donor is not accessible for immediate attachment after the purge cycle is complete. While it is perhaps physically impossible to maintain the needles in a completely sterile environment prior to their percutaneous entry into a patient or donor, it is highly desirable to minimize the time during which the needles are exposed to a nonsterile environment.

The present invention simultaneously accomplishes such goals in a dual needle type of system by commonly enclosing the collection and return needles in a sterile housing that can also be used to facilitate the purging cycle. Thus, saline liquid during the purge cycle is permitted to flow serially through the needles and the common enclosure, the air being then collected (or purged) in the enclosure itself and/or in a separate air trap location of the tubing network.

Even a single needle set may include a similar needle housing to facilitate purging—albeit the return fluid path could then be via a valved tubing branch or the like rather than via second regularly used needle/tubing branch as in a dual needle system, or could be returned cyclically via the singular tubing path is sufficient saline storage is made available in the needle housing.

The tubing network including the collection/return needles, their common enclosure and blood constituent processing devices (e.g., blood filters, platelet separators, etc.) can thus be manufactured as a unitary disposable unit which can be connected to an automatic blood processing unit prior to use. Moreover, since the tubing network will remain "closed" during the purge sequence, the tubing network is particularly adapted for automated purging of air. Once all air has been purged from the tubing network, the phlebotomist may wait until the patient/donor is at hand and prepared before separating the collection and/or return needle(s) from their enclosure and intravenously connecting them. The enclosure thus not only facilitates purging, it also maintains the needle(s) in a sterile environment to minimize the time interval in which the needles are exposed to a nonsterile environment.

The advantages and objects briefly mentioned above, as well as others, will be more clearly understood after careful consideration is given to the detailed descriptions of exemplary embodiments of this invention which follow.

BRIEF DESCRIPTION OF THE ACCOMPANYING DRAWINGS

Reference will hereinafter be made to the accompanying drawings wherein like reference numerals throughout the various FIGURES denote like structural elements and wherein.

DETAILED DESCRIPTION OF THE EXEMPLARY EMBODIMENTS

Figure 1:
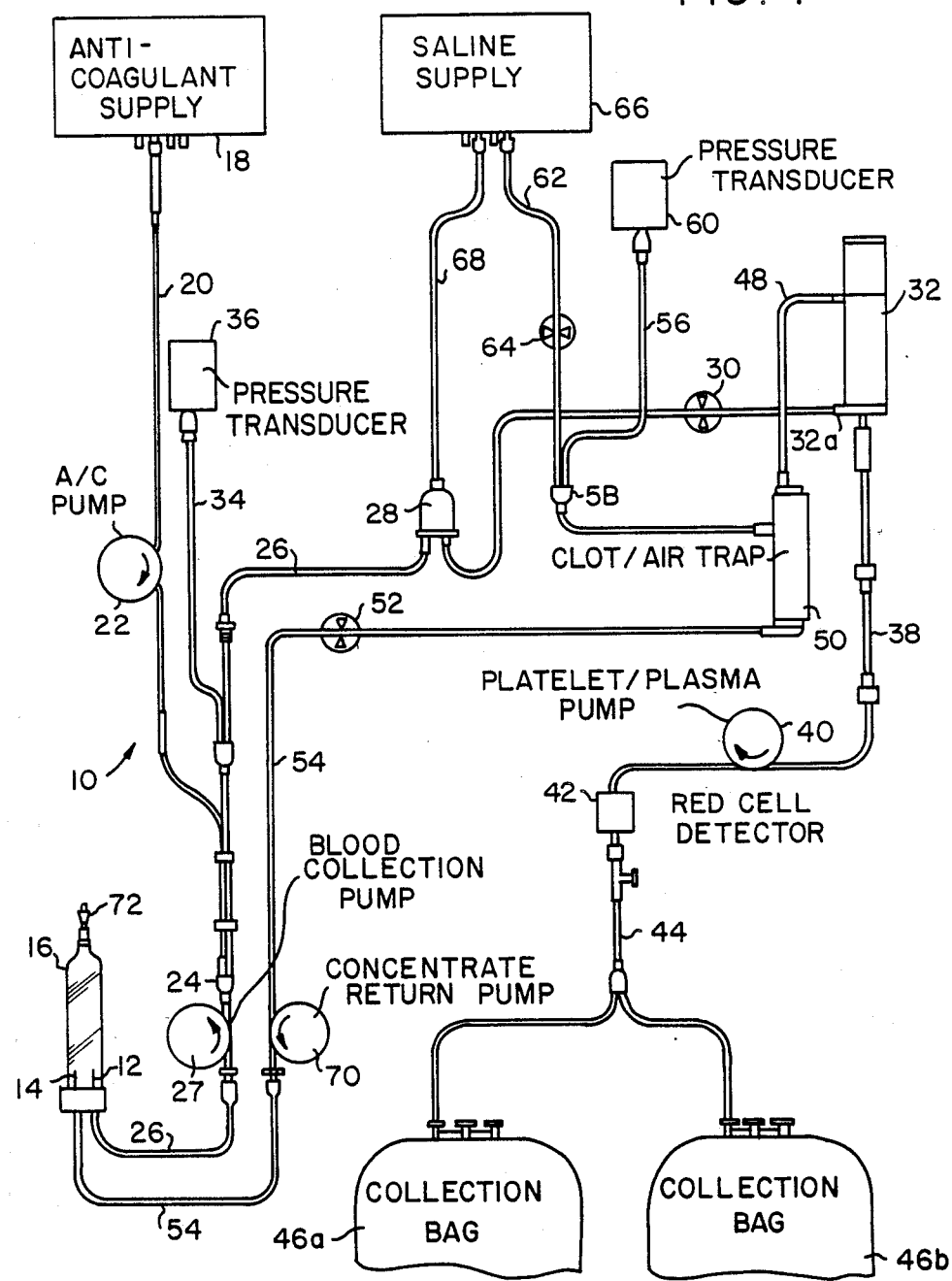
FIG. 1 is a schematic representation of a blood constituent processing system employing the present invention.

A blood constituent processing system 10 is shown in FIG. 1 as employing a tubing network having collection and return needles 12, 14, respectively, commonly housed within an enclosure 16. In the exemplary system of FIG. 1, two needles are employed—that is, one needle 12 is employed as a collection needle (used to collect whole blood from a patient or donor) and a second needle 14 is employed as a return needle (used to return residual/treated blood constituents to the donor through e.g., a vein located in a different part of the body from the location of collection needle 12). Additional needles may be employed and also commonly housed within enclosure 16 for other functions (e.g., monitoring the patient's or donor's pulse rate, blood pressure, etc., by means not shown in FIG. 1).

The entire fluid flow path (including all interconnecting tubing, the platelet separator/plasma filter and the like) is preferably defined by a disposable plastic tubing network or set which also includes the collection and return needles 12, 14 commonly housed within enclosure 16. The disposable tubing network is first manually inserted into an automatic blood processing apparatus 10 so as to be mechanically coupled to various computer-controlled peristaltic pumps, pressure sensors, electromagnetically operated clamps, and the like. The phlebotomist may, after priming, then withdraw needles 12, 14 from enclosure 16 and intravenously connect them to the patient/donor so that blood processing may commence.

During blood processing, an anticoagulant is typically fed from supply 18 through line 20 by controlled pump 22 into the drawn blood supply at a location 24 near the collection needle 12. Drawn blood is pumped through the collection needle 12 in line 26 by mean of controlled peristaltic blood pump 27, through an air bubble trap, an open blood clamp 30 and to the input side 32a of platelet separator/plasma filter device 32. A pressure transducer branch tubing 34 communicates with pressure transducer 36. The filtrate from separator/filter 32 may be pumped through line 38 by controlled peristaltic platelet/plasma pump 40 (or merely permitted to flow as the difference between the controlled flow rates of pumps 27 and 70 as should be apparent) and on through a photosensitive red cell detector 42 and tubing 44 to filtrate collection bags 46a and 46b.

The residual (e.g., concentrated) blood constituents from separator/filter 32 is pumped by concentrate return pump 70 to pass out through line 48, a blood clot pair trap 50, an open return clamp 52 and back to the return needle 14 via tubing 54. The pressure of return line 54 may be monitored via branch line 56 connected at junction 55 communicating with pressure transducer 60. A saline branch line 62 connects near junction 58 passing through electromagnetically controlled clamp 64 and back to the saline supply 66 (which is also connectable via tubing 68 to the filter trap 28 and, therefore, to the collection side of the fluid circuit).

Prior to actual blood processing and with the tubing set manually interconnected to the automatic processing apparatus 10, the phlebotomist may select an automatic priming sequence with common enclosure 16 still in place and enclosing collection and return needles 12, 14. During such initial priming procedures (which may include successive programmed pumping of saline solution bi-directionally throughout various parts of the system by an automated sequence control of pumps 22, 27, 40, 70 and of clamps 30, 52 and 64), the system of FIG. 1 primes the fluid circuit with saline solution from supply 18.

During the priming sequence, collection needle 12 and return needle 14 will remain housed within antiseptic enclosure 16. Enclosure 16 preferably includes a nonwettable microscopic air filter 72 which, when disposed vertically, permits any included air to exit from the system but which does not permit the entry of microbes nor the exit of saline solution from enclosure 16.

The saline solution from supply 66 may be pumped (in either direction) by the collection and/or return pumps 27, 70, respectively, around a fluid circuit in which the saline solution passes, among others, through the tubing 54 and return needle 14, the common enclosure 16, collection needle 12 and tubing 26.

Figure 2:
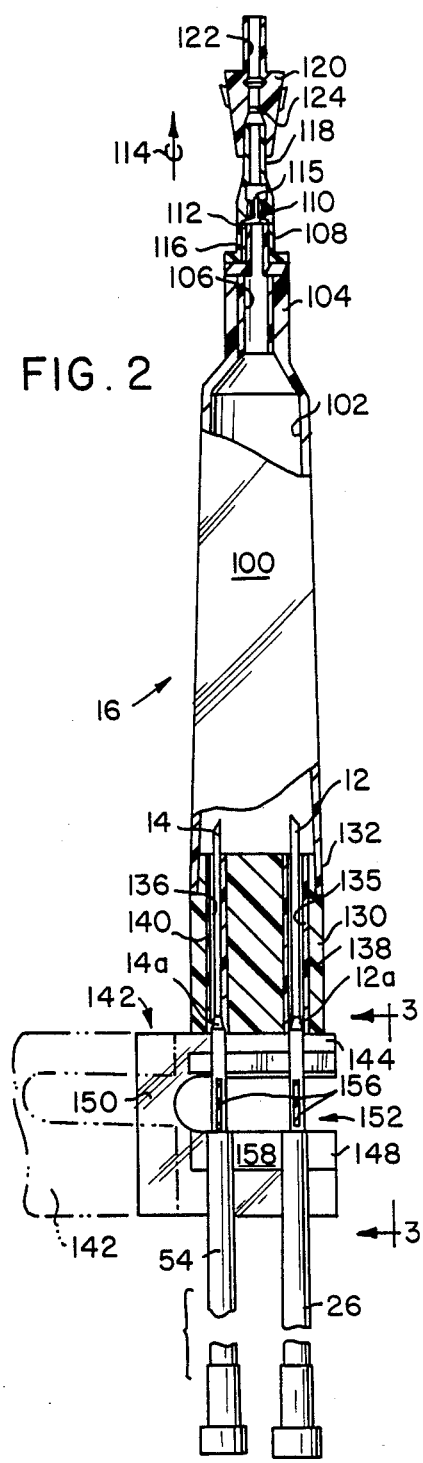
FIG. 2 is an elevational view, partly in section, of an exemplary embodiment of a dual needle housing/priming device in accordance with this invention.
Figure 3:
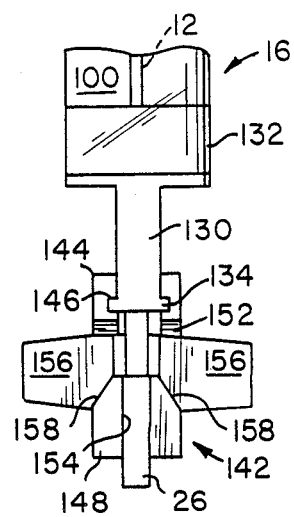
FIG. 3 is a detailed elevational view taken along line 3—3 in FIG. 2.

One preferred form of the common needle enclosure 16 is shown in accompanying FIGS. 2 and 3. Here, the needle enclosure 16 generally includes an elongate collection tube 100 defining an interior chamber 102. The distal end 104 of tube 100 also establishes a vent passageway 106 in fluid communication with interior chamber 102. A one-way valve member 108 (of a conventional variety) is axially fixed to distal end 104 and communicates with interior chamber 102. Valve 108 includes a plug member 110 which is displaceable upwardly from valve seat 112 when fluid flows from interior chamber 102 in the direction of arrow 114. Upon such an occurrence, the plug member 110 will be seated against protrusions 115 such that fluid communication is then established between upstream stem 116 and downstream stem 118. On the other hand, when fluid attempts to flow in the opposite direction, plug member 110 will once again be seated against valve seat 112 so as to prevent any fluid flow. Accordingly, one-way valve 108 only permits fluid (e.g., air and/or saline solution) to flow in the direction of arrow 114.

The upstream stem 118 preferably has a male leur-type taper so as to couple with a female leur-type taper on filter member 120. Filter member 120 defines an axial flow path 122 which communicates with chamber 102 via one-way valve 108 but which is interrupted by means of biological filter medium 124. Biological filter medium 124 may be a well-known conventional material which is pervious to air but impervious to microbes and/or liquid. The hydrophobic nature of filter 124 is advantageous in the FIG. 2 embodiment because air which enters chamber 102 via the collection and return needles 12, 14 may accumulate in the distal end 104 and pass (via one-way valve 108) into passageway 122 and through filter medium 124. Any saline solution, however, which may reach filter medium 124 during the priming sequence is prevented from discharge due to the hydrophobic nature of filter medium 124. Thus, the enclosure 16 conveniently automatically vents only air from the tubing network. At the same time, because at least two needles are involved in this embodiment (or because a temporary alternate flow path is provided if only a single needle system is involved), one may continue to have fluid flow within the network so as to move otherwise trapped air pockets to a discharge point (or to a proper air trap point).

A plug member 130 sealingly closes the proximal end 132 of enclosure 100 and, moreover, includes, at a lower end, a transverse flange 134 (as is seen more clearly by reference to FIG. 3). Plug member 130 also defines a pair of passageways 135, 136 permitting needles 12, 14 to access interior chamber 102. Of course, if needles additional to needles 12, 14 are required, plug 130 can be suitably modified to include further passageways to accommodate same.

Passageways 135, 136 may each include a liner 138, 140, respectively, of resilient material so as to provide sufficient compliance to sealingly engage proximal shoulders 12a, 14a of needles 12, 14. It should be noted that needles 12, 14 are coaxially positioned within passageways 135, 136 so as to be spaced from liners 138, 140. This is particularly advantageous since biological lubricants (.e.g., silicone) typically coated upon needles 12, 14 will not be removed when needles 12, 14 are withdrawn from passageways 135, 136, respectively.

A generally C-shaped coupling member 142 is provided to retain needles 12, 14 within enclosure 16 so as to prevent inadvertent separation. Coupling member 142 includes an upper leg 144 which defines a slot 146 for slidably receiving transverse flange 134. The slidable cooperation between slot 146 and flange 134 permits coupling member 142 to be moved from a coupled position with plug 130 (and thus enclosure 16 as shown in solid line in FIG. 2) to an uncoupled position (shown in chain line in FIG. 2). Coupling number 142 also includes a lower leg 148 integrally connected to upper leg 144 by means of lateral bridge portion 150 so as to define, together with upper leg 144, an open-ended transverse space 152. Lower leg 148 is itself split axially so as to define a transverse trough 154 (see FIG. 3).

Prior to use, it is important that the collection and return needles 12, 14, respectively, be maintained in the sterile environment of interior chamber 102 and thus, the prevention of inadvertent needle withdrawal is desirable. Coupling member 142 is one example of a structure to achieve such a function The collection and return needles 12, 14, in and of themselves, may be conventional and may include a pair of conventional grippable radial wings 156 to assist the phlebotomist in the manual manipulation thereof. Coupling member 142 accepts wings 156 within space 152 such that the lower edges of wings 156 bear against the lateral beveled edges 158 of lower leg 148. The tubing 26, 54 connected to the collection and return needles, respectively, is thus positioned within the trough 154 of the lower leg 148. In such a manner, the wings 156 preclude inadvertent withdrawal of the collection and return needles due to their bearing engagement with coupling member 142 when the latter is connected to flange 134. At the proper time, the phlebotomist can slidably remove coupling member 142 from flange 134 (a shown in chain line in FIG. 2) thereby permitting withdrawal of the collection and/or return needles 12, 14, respectively. As such, only a minimal time period is required in which the collection and return needles 12, 14 are exposed to a nonsterile environment.

Figure 4:
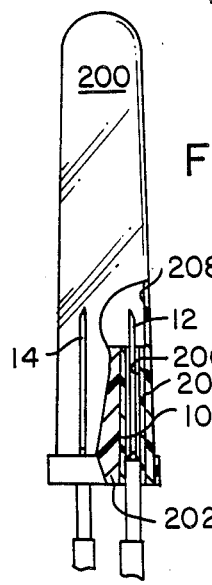
FIG. 4 is an elevational view, partly in section, showing another embodiment of the invention.
Figure 5:
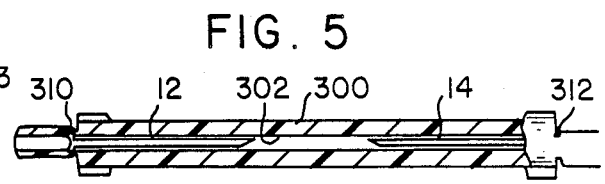
FIG. 5 is a cross-sectional view of a further embodiment of the invention.

FIGS. 4 and 5 each show further examples of the invention. The structure of FIG. 4 is similar to the structures shown and described above with respect to FIGS. 2 and 3 with the principal exception being that no vent passageway is provided in the distal end of tube 200. A plug member 202 sealably closes the proximal end of tube 200 and, like the embodiment of FIGS. 2 and 3, includes flexible liners 204 for passageways 206 so that needles 12, 14 are each in communication with chamber 208 of enclosure 200.

In FIG. 5, a common enclosure tube 300 is provided so that the collection and return needles 12, 14 are opposed to one another coaxially yet are each in fluid communication with interior chamber 302. In the embodiment of FIG. 5, final purging is preferably accomplished in the direction of expected later blood flow to better ensure that entrained air from the tubing network will not later enter the return line. Each of the needles 12, 14 is preferably integrally molded with enclosure tube 30 so as to provide unitary frangible coupling members 310, 312, respectively. Relative twisting between the needles 12, 14 and enclosure tube 300 will thus break the frangible couplings 310, 312 so that the needles 12 and 14 can be withdrawn from tube 300 and then intravenously connected to the patient. (The frangible couplings 310, 312 could also be provided with the embodiment of FIGS. 2-3 and FIG. 4, if desirable.) Enclosure tube 300 may be rigid or may be flexible, or may include a flexible central region for ease in packaging and tubing routing in use.

Each embodiment of this invention is particularly well suited for automated purging of air from a tubing network since a closed flowpath is provided through the needle(s) later to be used for intravenous connection.

The purging sequence may also include a temporary partial evacuation of the interior chamber defined by the needle enclosure by, for example, operating pump 27 in the proper direction with clamp 52 closed (see FIG. 1). This may be desirable, for example; to ensure a sufficient liquid column in the pressure transducer branch lines 34, 56. Thus, after drawing a slight vacuum (e.g., 50 mmHg), clamp 52 is released and saline purge solution from supply 66 will positively flow into the tubing system (including a portion of the pressure transducer branch lines). This type of vacuum priming procedure may also assist in filling enclosure 16 via needle 14 and thence on to line 26 via needle 12 to more efficaciously purge air from the tubing network. Air which is forcibly transferred into line 26, may then be conveniently trapped at a suitable location elsewhere in the tubing network, for example, by trap 28 and/or at the top of saline supply 66.

While the present invention has been described only with respect to a few exemplary embodiments, those in the art will recognize that many modifications may be made while yet retaining many of the novel features and advantages of this invention. Accordingly, the appended claims are intended to cover all such modifications.

What is claimed is:

1. A method for machine-automated purging of air or other gases from a tubing network containing liquid and having at least one tubular needle fluid connected at a terminal end thereof, said method comprising the steps of:

providing said needle in fluid communication with a chamber;

machine purging air or other gases from said network by automated machine pumping of said liquid into said chamber through said needle and then automated machine pumping at least some of said liquid from said chamber so that the extracted liquid is pumped back into said network, and cyclically repeating said two-way automated machine pumping of fluid flows sufficiently to insure that the tubing network is filled completely with said liquid.

2. A method for removing air trapped at discrete locations within a tubing system of the type having at least one pair of hollow needles, said method comprising the steps of:

(a) enclosing at least a distal region of said needles within a common chamber;

(b) flowing liquid through one portion of the tubing system and into said chamber via one of said needles; and (c) flowing liquid out from said chamber via the other of said needles whereby air in said tubing system is purged.

3. A method as in claim 2 further comprising the steps of collecting air in said chamber during said flowing step and venting said collected air from said chamber.

4. A method as in claim 2 wherein steps (b) and (c) are practiced concurrently.

5. A method as in claim 2 wherein steps (b) and (c) are practiced such that air introduced into said chamber via said one needle is also passed through and removed from said chamber via said other needle, collected and purged from the tubing in another location.

6. A method as in claim 7 wherein air is collected in a distal portion of said chamber during concurrent practice of steps (b) and (c).

7. A method for removing air trapped at discrete locations within a tubing system of the type having at least one pair of hollow needles, said method comprising the steps of:

(a) enclosing at least a distal region of said needles within a common chamber;

(b) flowing liquid through one portion of the tubing system and into said chamber via one of said needles; and (c) flowing liquid out from said chamber via the other of said needles whereby air in said tubing system is purged, wherein the tubing set includes a pressure transducing branch purposefully including a trapped air segment and wherein steps (b) and (c) are practiced by the sequential steps of:

(i) initially obstructing liquid flow via said one needle;

(ii) establishing a reduced pressure condition within said chamber and within a portion of said tubing system including said pressure transducing branch via said other needle; and then (iii) removing the liquid flow obstruction of step (i) to thereby allow liquid to flow into said chamber via said one needle and then on to said other portion of said tubing system via said other needle under influence of said reduced pressure condition establishing by step (ii) thereby ensuring at least a predetermined minimum column of liquid within said pressure transducing branch.

8. Apparatus to assist in the purging of air from a blood processing system comprising:

a tubing network having at least first and second hollow needles connected to first and second portions of the tubing network, respectively;

an enclosure defining an interior chamber; and coupling means for removably coupling said first and second needles with said enclosure such that common fluid communication between said chamber and the hollow of each said first and second needles is established to permit purging of air in said tubing network with a purge fluid.

9. Apparatus as in claim 8 wherein said coupling means includes frangible connecting means which, upon breakage, permit removal of said first and second needles from said enclosure.

10. A disposable, biologically, closed, apparatus for use in a blood processing system and designed to have air purged therefrom prior to actual use, said apparatus comprising:

blood collection and return needles;

a disposable tubing network having one portion in fluid communication with said collection needle and another portion in fluid communication with said return needle;

air trap means defining an interior chamber for commonly retaining said collection and return needles, prior to use, such that their respective cannulae communicate with said interior chamber, said air trap means operating to purge air entrained in a purge fluid flowing through said interior chamber via said collection and return needles.

11. A disposable tubing network particularly adapted for use in blood constituent processing applications, said network comprising:

a collection tube portion including a collection needle adapted for collecting blood constituents from a patient;

a return tube portion including a return needle adapted for returning blood constituents to a patient; and a disposable chamber for commonly retaining said collection and return needles in fluid communication prior to the time of actual usage in said blood processing applications.

12. Apparatus to trap and remove air from a tubing network adapted for blood constituent processing applications, said apparatus comprising:

at least one pair of cannular needles, each needle having a first-end fluid connected to said tubing network;

a trap housing having proximal and distal ends and defining therebetween an interior chamber;

coupling means for removably coupling the other ends of said pair of needles to said proximal end of said trap housing such that their cannulae directly communicate with said interior chamber; and vent means having a vent passageway in fluid communication with said interior chamber at said distal ends of said trap housing for venting air from said trap housing which accumulates in said interior chamber.

13. A device as in claim 12 wherein said vent means includes a porous biological filter medium which allows passage of air therethrough but yet substantially prevents passage of liquid.

14. A device as in claim 12 further comprising a one-way valve in said vent passageway which only permits fluid to flow in a venting direction from said interior chamber.

15. A device as in claim 14 wherein said one-way valve is positioned upstream of said vent means relative to said venting direction of fluid flow through said vent passageway.

16. Apparatus to trap and remove air from a tubing network adapted for blood constituent processing applications, said apparatus comprising:
at least one pair of cannular needles, each needle having a first-end fluid connected to said tubing network;
a trap housing having therebetween an interior chamber;
coupling means for removably coupling the other ends of said pair of needles to said proximal end of said trap housing such that their cannulae directly communicate with said interior chamber; and
vent means having a vent passageway in fluid communication with said interior chamber at said distal end of said trap housing for venting air from said trap housing which accumulates in said interior chamber;
each said needle including a radially extending pair of grip members, and wherein said coupling means includes:
a closure plug fixed to and closing said proximal end of said trap housing and including a transverse flange at a lower end thereof;
said closure plug having at least one pair of passageways extending axially relative to said trap housing, each for retaining a respective one of said needles such that said cannulae are in common fluid communication with said interior chamber;
each said passageway including compliant seal means for establishing a fluid seal with an external peripheral region of its respectively associated needle thereby sealing said interior chamber against infusion of ambient contaminants;
a generally C-shaped retaining member having a pair of separated arms defining a space therebetween, an upper one of said arms including a guide recess which slidably receives said flange to permit said retaining member to be slidably coupled to and removed from said closure plug;
said pair of grip members being disposed in said space defined between said pair of arms such that said grip members bear against a lower one of said arms when said retaining member is coupled to said trap housing to prevent inadvertent withdrawal of said needles from their respective passageways.

17. A disposable tubing network comprising:
at least one hollow needle fluid connected to at least one distal end of the tubing network; and
a housing removably disposed about the distal end of said needle and also in further fluid communication with said tubing network;
said housing including a biological hydrophobic filter for venting air from the housing while preventing the discharge of fluid therefrom and while also preventing the ingress of microbes to said housing.

18. A disposable tubing network as in claim 17 wherein said network includes two hollow needles, each being disposed at the distal end of corresponding tubing branches, the ends of both needles being commonly disposed within said housing thereby automatically providing said further fluid communication with said network.

19. A disposable tubing network as in claim 18 wherein said two needles are disposed at a first end of said housing and wherein an opposite second end of the housing includes a biological hydrophobic filter for venting air from the housing while preventing the discharge of fluid therefrom and while also preventing the ingress of microbes to said housing.

* * * * *